(12) United States Patent
Zeng et al.

(10) Patent No.: US 10,865,256 B2
(45) Date of Patent: Dec. 15, 2020

(54) METHOD FOR PREPARING CROSS-LINKED HYALURONIC ACID-BASED CELL SCAFFOLD MATERIAL

(71) Applicant: Hangzhou Singclean Medical Products Co., Ltd., Hangzhou, Zhejiang (CN)

(72) Inventors: Jin Zeng, Zhejiang (CN); Weiqing Sun, Zhejiang (CN)

(73) Assignee: Hangzhou Singclean Medical Products Co., Ltd., Hangzhou (CN)

( * ) Notice: Subject to any disclaimer, the term of this patent is extended or adjusted under 35 U.S.C. 154(b) by 0 days.

(21) Appl. No.: 16/289,666

(22) Filed: Mar. 1, 2019

(65) Prior Publication Data

US 2019/0270829 A1 Sep. 5, 2019

(30) Foreign Application Priority Data

Mar. 1, 2018 (CN) .......................... 2018 1 0170211

(51) Int. Cl.
| | | |
|---|---|---|
| *C08B 37/08* | (2006.01) | |
| *A61L 27/52* | (2006.01) | |
| *A61L 27/20* | (2006.01) | |
| *C08L 5/08* | (2006.01) | |

(52) U.S. Cl.
CPC .......... *C08B 37/0072* (2013.01); *A61L 27/20* (2013.01); *A61L 27/52* (2013.01); *C08L 5/08* (2013.01); *A61L 2400/18* (2013.01)

(58) Field of Classification Search
None
See application file for complete search history.

(56) References Cited

FOREIGN PATENT DOCUMENTS

| CN | 101367884 | * | 9/2008 |
|---|---|---|---|
| CN | 101367884 A | | 2/2009 |
| CN | 103613686 B | | 8/2015 |
| CN | 105969825 A | | 9/2016 |
| CN | 104910369 B | | 10/2017 |

* cited by examiner

*Primary Examiner* — Melissa S Mercier

(57) ABSTRACT

Disclosed is a method for preparing cross-linked hyaluronic acid-based cell scaffold material. The hyaluronic acid-based cell scaffold is obtained by subjecting a hyaluronic acid and a disulfide cross-linking agent to an amidation reaction, followed by dialysis-freeze drying. The cell scaffold has abundant pores, good mechanical strength which ensures that the scaffold does not rupture in transplantation, and good biocompatibility. The method is advantageous in that the raw material is easy to obtain, the reaction condition is moderate, and the process is simple. Cross-linked networks of the prepared hydrogel contain disulfide bonds, which can quickly split into single chains at the presence of small molecular glutathione. The hyaluronic acid-based cell scaffold has flexibly controllable mechanical property, disaggregation ability, and swelling property, and therefore has wide applications in facilitating cartilage injury repair, skin repair, cell culture, etc.

12 Claims, 1 Drawing Sheet

METHOD FOR PREPARING CROSS-LINKED HYALURONIC ACID-BASED CELL SCAFFOLD MATERIAL

CROSS REFERENCE TO RELATED APPLICATION

This application claims priority to Chinese Patent Application No. 201810170211.8 filed on Mar. 1, 2018, the entire contents of which are incorporated herein by reference.

FIELD OF THE INVENTION

The present application relates to the technical field of biomaterials, and in particular, to a method for preparing a reduction-responsive cross-linked hyaluronic acid-based cell scaffold material.

BACKGROUND OF THE INVENTION

Hyaluronic acid is a natural mucopolysaccharide existing in human skin for preserving moisture. It is a major component of cellular matrix and vitreous body. Hyaluronic acid is a linear polyanionic mucopolysaccharide formed by the alternate linking between (1-β-4) D-glucuronic acid (glucosamine) and (1-β-3) N-acetyl-D-glucose (glucuronic). It has an important physiological function in vivo due to its unique molecular structure and physicochemical properties. Hyaluronic acid is now widely used, mainly in the form of its sodium salts, in fields of cosmetics, clinical medicine, food, etc. High-purity hyaluronic acid has been widely used in ophthalmology, orthopedics, and anti-adhesion after surgery.

Hyaluronic acid can contribute significantly to the proliferation and migration of endothelial cells in aortic and capillary, protect granulation tissue against oxygen free-radical damage, and contribute to wound healing. However, the application prospect of hyaluronic acid is limited by its weak mechanical property and rapid degradation rate in vivo. For this reason, hyaluronic acid is usually modified by methods such as cross-linking, grafting, esterification, etc. Commonly used cross-linking methods at present include: physical cross-linking, for example by using sodium sulfate, sodium citrate, or sodium tripolyphosphate; chemical cross-linking, by using a cross-linking agent such as 1,4-butanediol diglycidyl ether (BDDE), 1,2,7,8-diepoxyoctane (DEO), divinyl sulphone (DVS), etc. These cross-linking methods control the cross-linking degree by regulating the concentration of the cross-linking agent and the cross-linking time, so as to prolong the existing time of hyaluronic acid in vivo. Hyaluronic acid products using divinyl sulphone and 1, 4-butanediol diglycidyl ether as a cross-linking agent have been widely used in treatment of orthopedic arthrophlogosis, operation anti-adhesion, soft tissue repair, and plastic and aesthetic filling, but their use in tissue engineering field is still being studied.

Due to its good biocompatibility which contributes to attachment and proliferation of seed cells, hyaluronic acid is usually used as a cell scaffold in tissue engineering. Tissue engineering requires that a scaffold material have good biocompatibility, suitable biodegradability, a three-dimensional porous structure which contributes to cell proliferation, and a certain degree of mechanical strength. When a hyaluronic acid scaffold is used to carry cells to repair a wound surface, after the seed cells are transplanted to the wound surface to be repaired, it would be ideal if the carrier material automatically degrades. However, in practice, because the hyaluronic acid after cross-linking needs more time to degrade, if the hyaluronic acid does not degrade or is removed in time, it will affect therapeutic effects. Besides, the removal of the carrier may cause cell loss and secondary damage to the wound surface. In order to solve these problems, an environment-responsive cell scaffold is prepared. The environment-responsive cell scaffold, in response to an external stimulus, can realize targeted delivery and release of drugs, and can be controlled to degrade, and thus has a wide range of applications in the future in drug delivery and tissue repairing.

A preferred method for the degradation of hyaluronic acid is biomacromolecular enzymolysis, which has high specificity, takes place in moderate reaction conditions, and is free of by-products. However, the limited source and high cost of hyaluronic acid enzyme restricts the application of hyaluronic acid enzyme. Disulfide bonds have good stimulus-responsive property, and can effectively break into thiol groups in a reducing condition; disulfide bonds are therefore introduced into the structure of the cross-linked hyaluronic acid. CN101367884 and CN103613686 disclose subjecting cysteamine and hyaluronic acid to an amidation reaction to obtain thiol-hyaluronic acid hydrogel containing thiol groups, followed by dissolution of the hydrogel and an oxidation reaction between the thiol groups, to the form disulfide bonds. The main principle of the foregoing is that thiol groups auto-oxidize in air to form thiol free-radicals, which collide with each other to form stable disulfide bonds. This process is, however, very slow and it takes a long time to form disulfide bonds. In order to accelerate the coupling of thiol groups, CN105969825 discloses using thiol-hyaluronic acid as a raw material, horseradish peroxidase as a catalyst, tyramine hydrochloride as an enzymatic substrate, to cross-link the thiol groups by inverse emulsion method at the presence of the catalyst horseradish peroxidase, to form disulfide bonds-containing hyaluronic acid hydrogel. In this method, residual organic solvent and residual nonionic surfactant may lead to toxicity in the use of the material. CN104910369 discloses subjecting an aldehyde hyaluronic acid and an amino/methylacryloyl bifunctional hyaluronic acid with a side chain containing disulfide bonds to a photopolymerization reaction, to obtain cross-linked hyaluronic acid hydrogel. The disulfide bonds can be effectively degraded at the presence of reducing small molecules, and the thoil-hyaluronic acid produced by the degradation can be absorbed quickly by an organism, which enables a culture system to have good biocompatibility.

Disulfide-containing cross-linked hyaluronic acids disclosed at present are usually used to prepare thoil-hyaluronic acids at the presence of dithiothreitol (DTT) for use in joint lubrication and cartilage repair. But preparation of disulfide bonds-containing cross-linked hyaluronic acid-based cell scaffolds for use in skin repair is seldom reported.

SUMMARY OF THE INVENTION

In tissue healing process, after cells migrate to a lesion area, it is required that a hyaluronic acid-based scaffold material gradually degrade and maintain the microenvironment for cell growth; besides, the degraded hyaluronic acid may facilitate the proliferation of the cells, and produce no by-product. Non-cross-linked hyaluronic acid hydrogel used as a cell scaffold has poor mechanical properties, and can cause rupture of the material during transplantation, and therefore cannot effectively carry cells for cell growth. Cross-linked hyaluronic acid has mechanical strength that increases with the increase of cross-linking degree, which prolongs the degradation time of the carrier scaffold, and after the migration of the cells, the residual material may affect skin repair.

In order to solve the problem of the incapability of controlling the degradation of hyaluronic acid in existing technologies, the present application aims to provide a method for preparing a reduction-responsive cross-linked hyaluronic acid-based cell scaffold material, which, at the presence of reducing small molecules, is capable of rapidly cleaving into single-chain hyaluronic acid which can be absorbed quickly by an organism. In order to achieve the above objective, the present application adopts the following technical solutions:

A method for preparing cross-linked hyaluronic acid-based cell scaffold material, characterized that 1-(3-dimethylaminopropyl)-3-ethylcarbodiimide hydrochloride (EDC.HCl) and N-hydroxysuccinimide (NHS) are added in sequence to an aqueous solution of hyaluronic acid having a pH value of 5.0-6.0, to form a mixture; the mixture is stirred at room temperature to obtain a uniform mixture; an aqueous solution of cystamine dihydrochloride is added to the uniform mixture to form a reaction system; the reaction system is adjusted to have a pH value of 5.0-6.0 for reaction; the reaction system after reaction is placed in a phosphate buffer for dialysis to form a dialyzed product; and the dialyzed product is freeze-dried to obtain a cross-linked hyaluronic acid-based cell scaffold.

In the method for preparing cross-linked hyaluronic acid-based cell scaffold material of the present application, the carboxyl group of the hyaluronic acid is first activated, and then an amidation reaction is carried out. The aqueous solution of hyaluronic acid is adjusted to have a pH value of 5.0-6.0, and NHS is used to activate the carboxyl group.

In the method for preparing cross-linked hyaluronic acid-based cell scaffold of the present application, the addition of cystamine dihydrochloride is performed after 1-(3-dimethylaminopropyl)-3-ethylcarbodiimide hydrochloride (EDC.HCl) and N-hydroxysuccinimide (NHS) has been mixed uniformly. Compared with the direct addition of the cystamine dihydrochloride to the reaction system, the addition of the cystamine dihydrochloride after the uniform mixing of EDC and NHS renders the reaction system more uniform and is thus more conducive to the cross-linking reaction. The addition of the aqueous solution of cystamine dihydrochloride is preferably performed dropwise.

An advantage of the present application is that different cross-linking controllable hyaluronic acids can be prepared in a one-step process to be used as a cell scaffold. The cell scaffold contains disulfide bonds, and can cleave at the presence of a reducing agent to generate thiol-hyaluronic acid which can be quickly absorbed by an organism. The cell scaffold also has good mucoadhesive property and in situ gelling property.

Further, the cell scaffold has a certain water absorption rate, and good mechanical strength, including tensile strength, tearing strength, elongation rate at break, elastic modulus, etc. In the process of preparing, carrying, transferring, and transplanting, the cell scaffold is not prone to rupture, and can be effectively used as a scaffold for cell growth.

The hyaluronic acid selected by the present application can be a metal salt of hyaluronic acid, which is, for example, one selected from the group consisting of sodium hyaluronate, potassium hyaluronate, calcium hyaluronate, and magnesium hyaluronate, or a mixture of any two of the foregoing, and is preferably sodium hyaluronate.

In the method of the present application, a molar ratio of —COOH in the hyaluronic acid to —$NH_2$ in the cross-linking agent is preferably in a range of 1:1-1:0.1, and a molar ratio of —COOH in the hyaluronic acid to EDC and NHS is preferably in a range of 1:0.1-0.6:0.1-1.

In the method of the present application, a reagent used for adjusting the pH value is an aqueous alkali or an acid solution. The aqueous alkali includes an aqueous solution of sodium hydroxide, potassium hydroxide, barium hydroxide, sodium carbonate, and is preferably sodium hydroxide, more preferably 0.1 M sodium hydroxide solution. The acid solution includes organic acid or inorganic acid, and is preferably hydrochloric acid, more preferably 0.1 M HCl.

In the method of the present application, after the addition of cystamine dihydrochloride, the reaction temperature is in a range of 0-10° C., preferably in a range of 1-4° C.

In the method of the present application, after the addition of cystamine dihydrochloride, the reaction time is 24-120 hours, preferably 72-96 hours. Preferably, cystamine dihydrochloride is added dropwise.

In the method of the present application, before the dialysis, the hyaluronic acid hydrogel is cut into small pieces having a weight in a range of 0.2-0.5 g for dialysis.

In the method of the present application, phosphate buffer is selected as a dialysate, and the phosphate buffer preferably contains 0.1-0.2 M phosphate and has a pH value of 7.0-7.4.

In the method of the present application, the dialysis time is 24-72 hours, preferably 48-72 hours.

In the method of the present application, the freeze-drying procedure includes: a first pre-freezing phase, wherein the dialyzed product is kept at a temperature ranging from −60° C. to −10° C. for 2-5 hours; a second sublimating phase, wherein the dialyzed product is kept at a temperature ranging from −40° C. to −25° C. for 4-8 hours and kept at a temperature ranging from −20° C. to 0° C. for 2-10 hours; and a third vacuum drying phase, wherein the dialyzed product is kept at a temperature ranging from 10° C. to 30° C. for 3-6 hours.

For the cross-linked hyaluronic acid-based cell scaffold material prepared by the method of the present application, its three-dimensional structure can quickly split at the presence of a reducing substance. The reducing small molecules selected may be dithiothreitol (DTT), glutathione (GSH) etc., and is preferably glutathione. Further, the concentration of the reducing small molecules is in a range of 0.1-10 mM.

The cross-linked hyaluronic acid-based cell scaffold material prepared by the method of the present application has a plurality of applications, including use as a cell scaffold for cartilage repair in tissue engineering, use as a cell scaffold for skin repair in tissue engineering, and use for targeted delivery of anti-cancer drugs.

In order to prepare a cell scaffold suitable for use in skin repair, the present application subjects hyaluronic acid of different molecular weights and a disulfide to a cross-linking reaction, followed by dialysis, and freeze-drying, to obtain a porous cell scaffold. The cell scaffold has certain degree of mechanical strength and exhibits controllable splitting rate at the presence of different concentrations of GSH, and is suitable for use in skin repair and for carrying seed cells to grow.

Compared with the existing technologies, the present application has the following beneficial effects.

The method for preparing cross-linked hyaluronic acid-based cell scaffold material provided by the present application uses a small molecule compound containing a disulfide bond as a cross-linking agent, and subjects it and the hyaluronic acid to an amidation reaction, to obtain disulfide bond-containing cross-linked hyaluronic acid hydrogel in a one-step process. The method is advantageous in that the raw material for the method is easy to obtain, the reaction condition thereof is moderate, and the process thereof is simple. By way of the amidation reaction, the hyaluronic acid is provided with a three-dimensional network structure in which the three-dimensional networks are connected to each other through chemical bonds; the hyaluronic acid therefore has good mechanical property and a uniform structure. A porous cell scaffold is obtained by freeze-drying the hydrogel.

The cross-linked hyaluronic acid-based cell scaffold provided by the present application has cross-linked networks containing reduction-responsive disulfide bonds, which degrades/disaggregates in response to an external stimulus. The cross-linked hyaluronic acid-based cell scaffold has a reducing disaggregation mechanism, excellent biocompatibility, good mechanical property, structural stability, flexible and controllable disaggregation ability. The mechanical property and the three-dimensional system of the cross-linked hyaluronic acid hydrogel prepared by the present application can therefore be effectively regulated and controlled. The cross-linked hyaluronic acid hydrogel can be used as a cell scaffold for in-vitro cell culture in tissue engineering, can be used in cell transplantation as well as tissue and cartilage repair, and has wide applications in the future in biomedical field.

The cross-linked hyaluronic acid-based cell scaffold prepared by the method of the present application can be used as a cell scaffold for cartilage repair in tissue engineering, and can be used a carrier scaffold for in-vitro culture of human or animal cartilage cells, for example for use in repair of cleft lip and palate.

The cross-linked hyaluronic acid-based cell scaffold prepared by the method of the present application can be used as a scaffold for in-vitro cell culture for skin repair in tissue engineering, can be used for the preparation of tissue engineered epidermis of epidermal cells, melanocytes, and fibrocytes, and for the repair of leucoderma and burn wounds.

The cross-linked hyaluronic acid-based cell scaffold prepared by the method of the present application can be used for the carrying, delivery, and intelligent release of anticancer drugs.

DETAILED DESCRIPTION OF THE EMBODIMENTS

The present application could be further understood from the following specific embodiments, which, however, are not intended to limit the present application.

I. Preparation of Cross-Linked Hyaluronic Acid-Based Cell Scaffold Material

Figure 1:
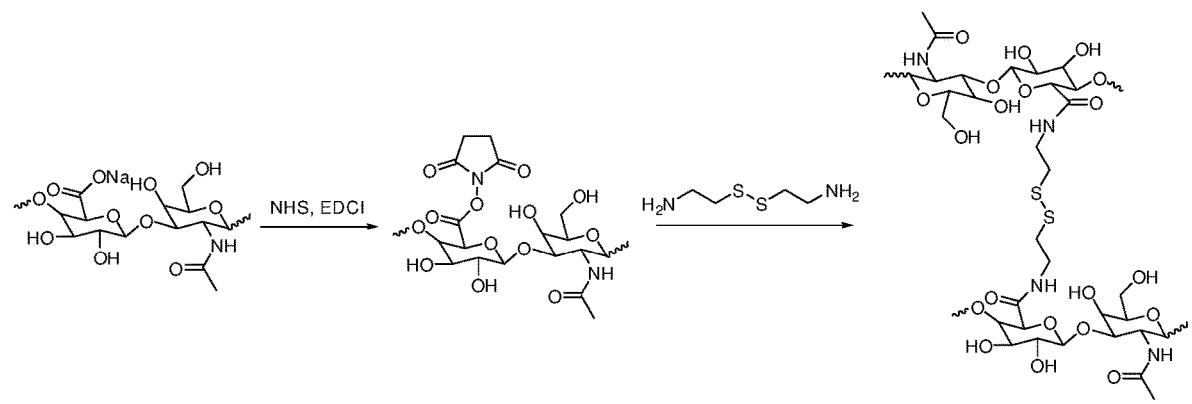
FIG. 1 shows a route diagram of preparing cross-linked hyaluronic acid according to the present application.

FIG. 1 shows a route diagram of preparing cross-linked hyaluronic acid according to the present application.

Example 1

Hyaluronic acid (1 g, having 2.48 mmol of —COOH) (injectable grade, molecular weight thereof being 0.9-1.1 million) was dissolved in 100 mL of deionized water. The resultant solution was adjusted to have a pH value of 5.0, followed by sequential addition of 0.475 g of 1-(3-dimethylaminopropyl)-3-ethylcarbodiimide hydrochloride (EDC), and 0.285 g of N-hydroxysuccinimide (NHS). The resultant mixture was stirred at room temperature for 3 hours. Cystamine dihydrochloride (0.153 g, 0.99 mmol) was dissolved in 5 mL of water to form a solution, which was added dropwise to the reaction system. After the dropwise addition of the solution, the resultant mixture was readjusted to have a pH value of 5.0-5.5, stirred at 4° C. to react for 96 hours. After that, the resultant mixture was placed in a phosphate buffer having a pH value of 7.4 for dialysis for 72 hours, pre-freezed at −50° C. for 3 hours, maintained at −30° C. for 6 hours, maintained at −15° C. for 8 hours, and then dried at 25° C. in vacuum for 4 hours, to produce a cross-linked hyaluronic acid-based cell scaffold (First Group: 1-1).

Example 2

Hyaluronic acid (1 g, having 2.48 mmol of —COOH) (injectable grade, molecular weight thereof being 0.9-1.1 million) was dissolved in 80 mL of deionized water. The resultant solution was adjusted to have a pH value of 5.0, followed by sequential addition of 0.380 g of 1-(3-dimethylaminopropyl)-3-ethylcarbodiimide hydrochloride (EDC), and 0.228 g of N-hydroxysuccinimide (NHS). The resultant mixture was stirred at room temperature for 2.5 hours. Cystamine dihydrochloride (0.115 g, 0.74 mmol) was dissolved in 5 mL of water to form a solution, which was added dropwise to the reaction system. After the dropwise addition of the solution, the resultant mixture was readjusted to have a pH value of 5.0-5.5, stirred at 4° C. to react for 90 hours. After that, the resultant mixture was placed in a phosphate buffer having a pH value of 7.4 for dialysis for 65 hours, pre-freezed at −50° C. for 2 hours, maintained at −30° C. for 5 hours, maintained at −15° C. for 8 hours, and then dried at 25° C. in vacuum for 4 hours, to produce a cross-linked hyaluronic acid-based cell scaffold (Second Group: 1-2).

Example 3

Hyaluronic acid (1 g, having 2.48 mmol of —COOH) (injectable grade, molecular weight thereof being 1.7-1.9 million) was dissolved in 60 mL of deionized water. The resultant solution was adjusted to have a pH value of 5.0, followed by sequential addition of 0.285 g of 1-(3-dimethylaminopropyl)-3-ethylcarbodiimide hydrochloride (EDC), and 0.171 g of N-hydroxysuccinimide (NHS). The resultant mixture was stirred at room temperature for 3 hours. Cystamine dihydrochloride (0.076 g, 0.49 mmol) was dissolved in 5 mL of water to form a solution, which was then added dropwise to the reaction system. After the dropwise addition of the solution, the resultant mixture was readjusted to have a pH value of 5.0-5.5, stirred at 4° C. to react for 85 hours. After that, the resultant mixture was placed in a phosphate buffer having a pH value of 7.4 for dialysis for 60 hours, pre-freezed at −50° C. for 3 hours, maintained at −30° C. for 6 hours, maintained at −15° C. for 6 hours, and then dried at 25° C. in vacuum for 4 hours, to produce a cross-linked hyaluronic acid-based cell scaffold (Third Group: 1-3).

Example 4

Hyaluronic acid (1 g, having 2.48 mmol of —COOH) (injectable grade, molecular weight thereof being 1 million) was dissolved in 50 mL of deionized water. The resultant solution was adjusted to have a pH value of 5.0, followed by sequential addition of 0.190 g of 1-(3-dimethylaminopropyl)-3-ethylcarbodiimide hydrochloride (EDC), and 0.114 g of N-hydroxysuccinimide (NHS). The resultant mixture was stirred at room temperature for 1.5 hours. Cystamine dihydrochloride (0.038 g, 0.25 mmol) was dissolved in 5 mL of water to form a solution, which was then added dropwise to the reaction system. After the dropwise addition of the solution, the resultant mixture was readjusted to have a pH value of 5.0-5.5, stirred at 4° C. to react for 80 hours. After that, the resultant mixture was placed in a phosphate buffer having a pH value of 7.4 for dialysis for 54 hours, prefreezed at −50° C. for 2 hours, maintained at −30° C. for 4 hours, maintained at −15° C. for 6 hours, and then dried at 25° C. in vacuum for 4 hours, to produce a cross-linked hyaluronic acid-based cell scaffold (Fourth Group: 1-4).

II. Measurement of Thickness and Pore Diameter of the Cross-Linked Hyaluronic Acid-Based Cell Scaffold Method: The scaffold material was cut into small pieces, and thickness of the material was measured using a vernier caliper. Results showed that with the increase of the feeding amount of the cross-linking agent, the thickness of the material gradually increased. When the content of the cross-linking agent was relatively high, the obtained cell scaffold had a uniform thickness and uniform pore diameters. But when the content of the cross-linking agent was too high, the obtained cell scaffold had very small pore diameters, which was not conducive to the exchange of nutrient substances during the culturing of cells. When the content of the cross-linking agent was relatively low, the cell scaffold obtained after freezing and drying had a non-uniform thickness, and in particular had relatively large pore diameters (some even reaching over 400 μm) at relatively thin locations of the scaffold, as a consequence of which the material had a relatively weak strength and the scaffold was thus prone to rupture. Therefore, it was concluded from the thickness and pore diameter of the material that, when the proportion of the cross-linking agent was suitable, the prepared material had a uniform pore diameter with a suitable size, in which case the material, by taking advantage of cell proliferation and growth, was capable of providing a microenvironment for cell growth.

TABLE 1

Thickness and Pore diameter of the cross-linked hyaluronic acid-based cell scaffold produced in Examples 1 to 4

| Sample No. | Molar Ratio (—COOH:—NH$_2$) | Thickness (mm) | Pore diameter (μm) |
|---|---|---|---|
| 1-1 | 1:0.8 | 1.14 ± 0.15 | 100 ± 16 |
| 1-2 | 1:0.6 | 1.36 ± 0.34 | 121 ± 38 |
| 1-3 | 1:0.4 | 1.92 ± 0.81 | 136 ± 21 |
| 1-4 | 1:0.2 | 2.03 ± 0.96 | 153 ± 42 |

III Measurement of Mechanical Strength of the Cross-Linked Hyaluronic Acid-Based Cell Scaffold Method: The cross-linked hyaluronic acid-based cell scaffold produced in Examples 1 to 4 was cut into 3×3 cm small pieces, and tensile property of the produced material was measured using a tensile machine. Results showed that, when the proportion of the disulfide cross-linking agent was relatively large, the prepared scaffold material had a relatively high mechanical strength. The scaffold material ruptures when the tensile force was 8-9 N, which ensured that when the cross-linked hyaluronic acid-based cell scaffold prepared by the method according to the present application was transferred and cut in the process of cell transplantation, the material did not break or rupture; the cross-linked hyaluronic acid-based cell scaffold could therefore be used as a scaffold for cell growth and provided a microenvironment for cell growth. But when the cross-linking degree was low, the scaffold material had a non-uniform thickness, in which case, the material ruptures at relatively thick locations when the tensile force was 4-5 N, and ruptures at relatively thin locations when the tensile force was 3-4 N. The larger the molecular weight of the hyaluronic acid was, the larger the tensile strength thereof was, as shown by sample 1-2 and sample 1-3.

TABLE 2

Tensile strength of the cross-linked hyaluronic acid-based cell scaffold prepared in Examples 1-4

| Sample No. | Molar Ratio (—COOH:—NH$_2$) | Tensile Strength (N) |
|---|---|---|
| 1-1 | 1:0.8 | 8.5 ± 0.9 |
| 1-2 | 1:0.6 | 7.3 ± 1.2 |
| 1-3 | 1:0.4 | 6.8 ± 1.5 |
| 1-4 | 1:0.2 | 4.8 ± 1.8 |

IV Expansion Rate and Water Absorption Rate of the Cross-Linked Hyaluronic Acid-Based Cell Scaffold Method of measuring expansion rate: The cross-linked hyaluronic acid-based cell scaffold produced in Examples 1 to 4 was cut into 3×3 cm small pieces. The small piece was put into 30 mL of 0.9% sodium chloride solution, and placed in a water bath at 37° C. for 2.5 hours. The length and width of the piece was then measured. The expansion rate was the percentage ratio of the length multiply by the width after the swelling to the length multiply by the width before the swelling.

Method of measuring water absorption rate: The cross-linked hyaluronic acid-based cell scaffold produced in Examples 1 to 4 was cut into 2×2 cm small pieces. The small piece was weighed and the weight thereof was recorded as $W_1$. The small piece was put into 20 mL of 0.9% sodium chloride solution at 37° C. for 10 minutes, taken out using a pair of tweezers, followed by removing unnecessary moisture from its surface, and then weighed and the weight thereof was recorded as $W_2$. The water absorption rate was the ratio of the weight of water absorbed by the scaffold material during a certain period of time to the weight of the scaffold material per se.

TABLE 3

Expansion rate and water absorption rate of the cross-linked hyaluronic acid-based cell scaffold produced in Examples 1 to 4

| Sample No. | Molar Ratio (—COOH:—NH$_2$) | Expansion Rate (%) | Water Absorption Rate |
|---|---|---|---|
| 1-1 | 1:0.8 | 94.9 ± 4.3 | 43.2 ± 1.5 |
| 1-2 | 1:0.6 | 99.8 ± 2.9 | 52.3 ± 2.1 |
| 1-3 | 1:0.4 | 103.6 ± 1.9 | 56.7 ± 3.5 |
| 1-4 | 1:0.2 | 113.5 ± 6.3 | 78.4 ± 2.6 |

V Reducing Property of Cross-Linked Hyaluronic Acid Hydrogel

Method: The cross-linked hyaluronic acid-based scaffold material (1-2) was cut into small pieces, from which three parts were weighed. Each part weighed 10 mg. PBS solution (pH=7.4) having 0.1 mM of GSH, PBS solution (pH=7.4) having 2 Mm of GSH, and PBS solution (pH=7.4) having 10 mM of GSH were added into the three parts, respectively.

The resultant solutions were placed in a thermostatic water bath at 37° C. under magnetic stirring. After the reaction was carried out for a certain period of time, the content of free hyaluronic acid after cleavage was determined, and the content of uronic acid was determined by measuring and diluting 1 mL of supernatant.

Figure 2:
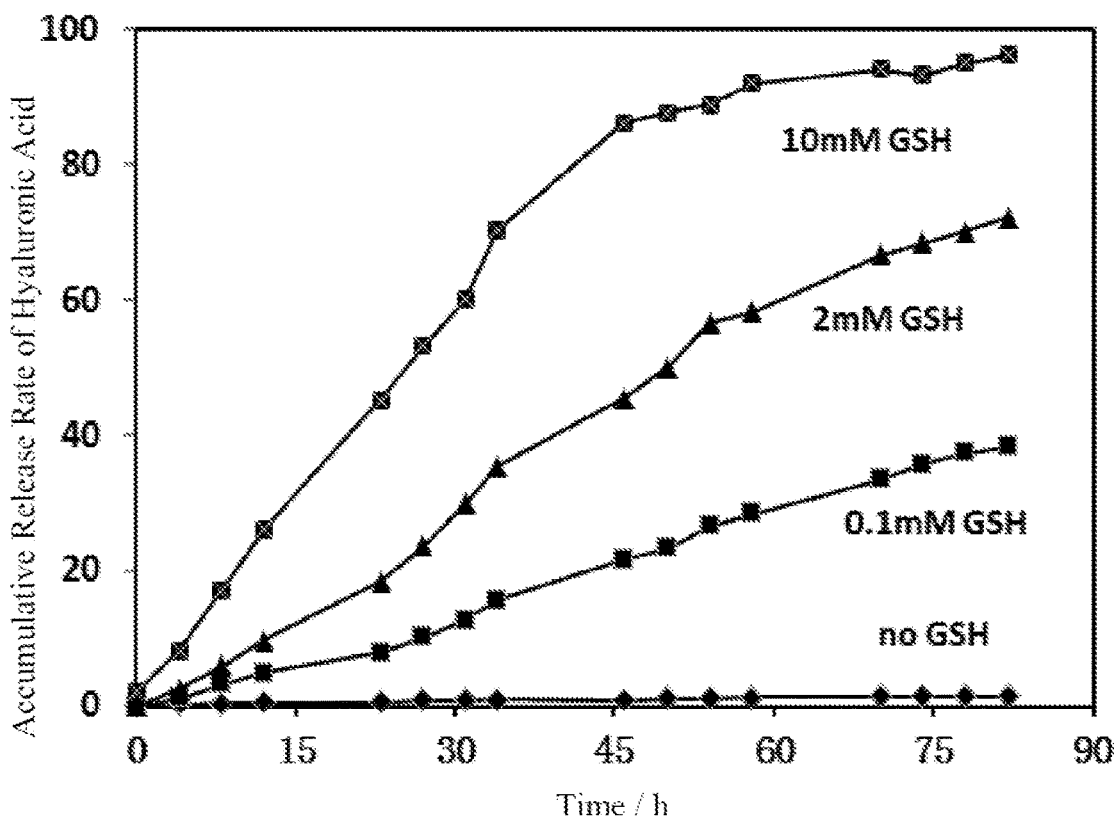
FIG. 2 shows reduction-responsiveness of cross-linked hyaluronic acid-based cell scaffold material prepared according to Example 2 of the present application.

GSH (glutathione) is considered to be the most important oxidation-reduction couple in animal cells. It determines the antioxidant ability of cells. The introduction of GSH does not lead to cytotoxicity, and therefore the cleavage of the carrier scaffold does not adversely influence the growth of cells. The free hyaluronic acid produced by the cleavage of the cross-linked hyaluronic acid-based scaffold was measured under the condition that concentrations of GSH were 0.1 mM, 2 mM, and 10 mM, respectively, and a phosphate buffered solution having a pH value of 7.4 was used as a control. Results are shown in FIG. 2, and indicate that under a reducing condition, the cross-linked hyaluronic acid-based scaffold can gradually decompose with the passage of time, until it becomes a solution. In addition, the larger the concentration of the reducing agent, the faster the three-dimensional structure of the produced scaffold material decomposes. A new approach is thus provided for the removal/decomposition of scaffold material after cells are transplanted to a wound surface in in-vitro cell culture and cell transplantation of tissue engineering study.

VI Cytotoxicity of Cross-Linked Hyaluronic Acid Hydrogel-Based Cell Scaffold Material MTT Assay In accordance with Biological Evaluation of Medical Devices—Part 5: Tests for In Vitro Cytotoxicity, the produced cross-linked hyaluronic acid hydrogel-based cell scaffold was cut into small pieces having a dimension of 0.1-0.3×0.1-0.3. Then, 1 g of the small pieces was measured and added to 1 mL of a cell culture liquid, and placed at a temperature of 37±2° C. for 30 hours. The leaching liquid was diluted with a culture medium, to obtain a series of diluted leaching liquids as test solutions. Results are shown in Table 5.

TABLE 5

Cytotoxicity of cross-linked hyaluronic acid-based cell scaffold prepared in Examples 1 to 4

| Samples | Cytotoxic Reactions |
|---|---|
| 1-1 | Grade 0 |
| 2-1 | Grade 0 |
| 3-1 | Grade <1 |
| 4-1 | Grade <1 |

The above results show that the cross-linked hyaluronic acid-based cell scaffold material prepared according to the present application has excellent properties, especially in material pore diameter, expansion rate, and water absorption rate. Furthermore, the prepared cross-linked hyaluronic acid-based cell scaffold has good biocompatibility and good reduction-responsiveness. Therefore, the cross-linked hyaluronic acid-based cell scaffold of the present application can be used in the culture of in-vitro cells in cartilage/skin repair, and can also be used to carry an anti-cancer drug to a specific site for intelligent release of the anti-cancer drug.

The above embodiments are merely for illustrating the principles of the present application, and are not intended for limiting the present application. Various variations and modifications can be made to the present application within the spirit and scope defined by the claims of the present application, and all such variations and modifications shall fall within the protection scope of the present application.

The invention claimed is:

1. A method for preparing a cross-linked hyaluronic acid-based cell scaffold material, comprising the steps of:
   adding 1-(3-dimethylaminopropyl)-3-ethylcarbodiimide hydrochloride (EDC.HCl) and N-hydroxysuccinimide (NHS) in sequence to an aqueous solution of hyaluronic acid having a pH value of 5.0-6.0, to form a mixture;
   stirring the mixture at room temperature to obtain a uniform mixture;
   adding an aqueous solution of cystamine dihydrochloride to the uniform mixture to form a reaction system;
   adjusting the reaction system to have a pH value of 5.0-6.0 for reaction;
   placing the reaction system after reaction in a phosphate buffer for dialysis to form a dialyzed product; and
   freeze-drying the dialyzed product to obtain the cross-linked hyaluronic acid-based cell scaffold,
   wherein the step of freeze-drying comprises: at a first pre-freezing phase, keeping the dialyzed product at a temperature ranging from −60° C. for 2-5 hours; at a second sublimating phase, keeping the dialyzed product at a temperature ranging from −40° C. to −25° C. for 4-8 hours and keeping at a temperature ranging from −20° C. to 0° C. for 2-10 hours; and at a third vacuum drying phase, keeping the dialyzed product at a temperature ranging from 10° C. to 30° C. for 3-6 hours.

2. The method according to claim 1, wherein a molar ratio of —COOH in the hyaluronic acid to —NH$_2$ in the cross-linking agent is in a range of 1:1-1:0.1, and a molar ratio of —COOH in the hyaluronic acid to EDC and NHS is in a range of 1:0.1-0.6:0.1-1.

3. The method according to claim 1, wherein the reaction is carried out at a temperature in a range of 0-10° C.

4. The method according to claim 1, wherein the reaction is carried out for 24-120 hours.

5. The method according to claim 1, wherein an aqueous alkali or an acid solution is used for adjusting the pH value.

6. The method according to claim 1, wherein hyaluronic acid based cell scaffold is cut into small pieces having a weight in a range of 0.2-0.5 g for conducting the dialysis.

7. The method according to claim 1, wherein the phosphate buffer contains 0.1-0.2 M phosphate and has a pH value of 7.0-7.4.

8. The method according to claim 1, wherein the dialysis is conducted for 24-72 hours.

9. The method according to claim 3, wherein the reaction is carried out at a temperature in a range of 1-4° C.

10. The method according to claim 4, wherein the reaction is carried out for 72-96 hours.

11. The method according to claim 5, wherein the aqueous alkali is 0.1 M sodium hydroxide solution, and the acid solution is 0.1 M HCl.

12. The method according to claim 8, wherein the dialysis is conducted for 48-72 hours.

* * * * *